(12) United States Patent
Biedermann et al.

(10) Patent No.: US 6,176,882 B1
(45) Date of Patent: Jan. 23, 2001

(54) INTERVERTEBRAL IMPLANT

(75) Inventors: Lutz Biedermann, VS-Villingen;
Thomas Wichmann, Hofstetten;
Jürgen Harms, Waldbronn, all of (DE)

(73) Assignee: Biedermann Motech GmbH,
Schwenningen (DE)

( * ) Notice: Under 35 U.S.C. 154(b), the term of this patent shall be extended for 0 days.

(21) Appl. No.: 09/403,125

(22) PCT Filed: Feb. 19, 1999

(86) PCT No.: PCT/EP99/01099

§ 371 Date: Oct. 14, 1999

§ 102(e) Date: Oct. 14, 1999

(87) PCT Pub. No.: WO99/42062

PCT Pub. Date: Aug. 26, 1999

(30) Foreign Application Priority Data

Feb. 20, 1998 (DE) .............................................. 198 07 236

(51) Int. Cl.[7] ....................................................... A61F 2/44
(52) U.S. Cl. .................................... 623/17.15; 623/17.11
(58) Field of Search ................................ 623/17, 17.15, 623/17.11; 606/61

(56) References Cited

U.S. PATENT DOCUMENTS

| | | | |
|---|---|---|---|
| 4,401,112 | * | 8/1983 | Rezaiman ............................... 623/17 |
| 5,522,899 | * | 6/1996 | Michelson ............................. 623/17 |
| 5,609,635 | * | 3/1997 | Michelson ............................. 623/17 |
| 5,658,335 | * | 8/1997 | Allen ..................................... 623/17 |
| 5,665,122 | * | 9/1997 | Kambin ................................. 606/61 |
| 5,893,889 | * | 4/1999 | Harrington ............................ 623/17 |

FOREIGN PATENT DOCUMENTS

| | | |
|---|---|---|
| 3608163 A1 | 9/1987 | (DE) . |
| 4447057 A1 | 4/1996 | (DE) . |
| 19529605 C2 | 2/1997 | (DE) . |
| 19549426 C2 | 2/1997 | (DE) . |
| 29623362 U1 | 5/1998 | (DE) . |
| 0635246 A1 | 1/1995 | (EP) . |
| 0637439 A1 | 2/1995 | (EP) . |
| 0734702 A1 | 10/1996 | (EP) . |
| 2717068 | 9/1995 | (FR) . |
| WO 97/00054 | 1/1997 | (WO) . |
| WO 97/06753 | 2/1997 | (WO) . |
| WO 97/15248 | 3/1997 | (WO) . |
| WO 98/48739 | 11/1998 | (WO) . |

* cited by examiner

Primary Examiner—Paul J. Hirsch
(74) Attorney, Agent, or Firm—Dike, Bronstein, Roberts and Cushman, LLP; George W. Neuner

(57) ABSTRACT

The invention relates to an intervertebrae implant comprising two side walls (1, 2) arranged at a distance to each other, a front wall (3) connecting the same at their one end, a back wall (4) connecting the same at their opposite other end, and one opening each on the base and cover part extending at right angles to the afore-mentioned walls. The invention also comprises at least one element (60, 61) provided for in the space (5) enclosed by the above walls, which element has a surface pointing towards the base or cover part and can be moved back and forth between a first final position in which said surface projects at least partly outwards beyond the base or cover part and a second final position in which the surface does not project beyond the base or cover part.

20 Claims, 5 Drawing Sheets

FIG.1

INTERVERTEBRAL IMPLANT

The invention relates to an intervertebrae implant comprising two spaced side walls, a front wall connecting the side walls at one end thereof, a back wall connecting the side walls at their other end and corresponding apertures in the bottom and top face lying transversely to the aforementioned walls.

Such an implant is inserted after removal of an intervertebral disk for stabilizing the intervertebral region until bone material which is filled in at the same time has grown to an osseous connection and strengthening.

An intervertebrae implant is disclosed in DE 195 29 605 C2. The implant comprises two hook-shaped portions initially bent back into a cavity which are moved out into an engagement position by screwing-in a screw having a wedge-shaped portion after inserting the implant in-between two vertebrae. It is a disadvantage of this apparatus that the gripper arms cannot be brought back into their retracted position, whereby the surgeon cannot change the position of the implant after having once extended the grippers.

The DE 195 49 426 C2 discloses an intervertebrae implant wherein two terminal portions of a hollow body are moved from an initially redressed position into an extended position by insertion of a screw having a truncated conical portion. Teeth provided at the outer faces engage the adjacent vertebrae in the extended position of the implant. There is the same drawback that the teeth, after initial extension and engagement with the adjacent vertebrae, cannot be retracted for replacement or readjustment.

From U.S. Pat. No. 5,522,899 an intervertebrae implant is known. This implant comprises a lower part being formed of a rectangular-shaped bottom with two side walls extending therefrom at right angles, the side walls being rectangular-shaped and having in their middle region, respectively, a projecting tongue extending away from the bottom. Further, an upper part is provided having a corresponding rectangular-shaped bottom and two side walls extending therefrom to the lower part at right angles, each having a portion for accomodating the tongues of the lower part. The sides of the bottoms facing each other, respectively, are wedge-segment-shaped and have such a size that between the bottoms facing each other a free space is formed. In this free space two wedges are provided having their basis opposite to each other and comprising bores being concentric to each other. The bore of the first wedge is without a thread and serves as guidance for a screw, whereas the bore of the second wedge comprises an internal thread which corresponds to the thread of the screw.

The length of the screw is selected so as to be passed through the first wedge and to be screwed in the second part if both wedges are in their position having the largest distance, in which said two wedge-shaped elements are positioned in their smallest distance to each other. By rotating the screw the second wedge is pulled in direction to the first wedge so as to enlarge the distance of the two wedge-shaped elements. As a result thereof the free end of the screw comes out from the second wedge. Since the screw itself is not guided in its positions with respect to the other elements, the movement of the two parts relative to the other elements is also not predetermined in a force-locking or form-locking manner, respectively.

It is the object of the invention to provide an improved intervertebrae implant of the initially described kind.

This object is achieved by an intervertebrae implant as defined in claim 1.

Further embodiments of the invention are defined in the subclaims.

The adjustable inward and outward displacement of the teeth allows for an individual adjustment to the prevailing an atomic shape of the end plates of the vertebrae. Moreover, the spacing of the vertebrae can be controlled by adjustment of this displacement of the teeth.

Further features and advantages of the invention will be apparent from the description of embodiments with reference to the Figures. In the Figures:

FIG. 1 is a perspective view of a first embodiment of a intervertebrae implant in exploded representation;

Figure 1:
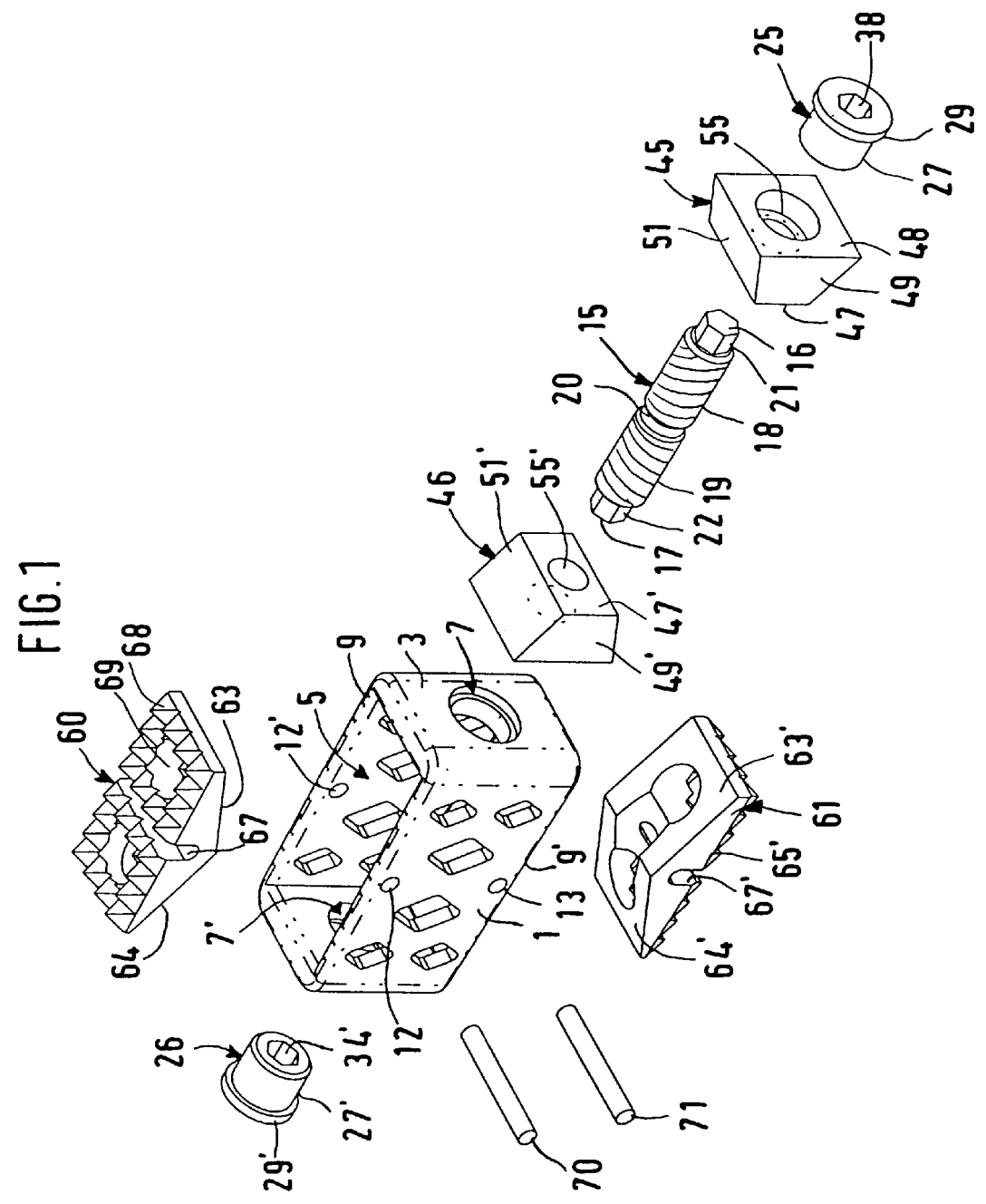
Figure 5:
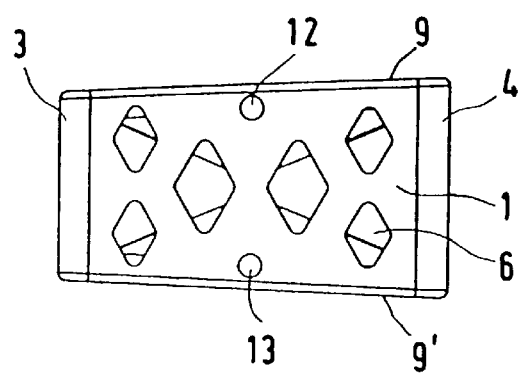
FIG. 5 is a side view of the intervertebrae implant.

As best shown in the FIGS. 1 and 4 to 6 the implant comprises a first side wall 1, a second side wall 2 spaced from the first side wall and a front wall 3 connecting the two side walls 1, 2 at their one end as well as a back wall 4 opposite to the front wall for connecting the two side walls at their opposite other ends. As best shown in FIG. 1 the bottom and top faces are open so that the four walls define a cavity 5 having an open bottom and an open top. As best seen in FIG. 5 the two side walls 1 and 2 have a plurality of apertures 6 which are preferably diamond-shaped and distributed over the side wall surfaces.

As best shown in the FIGS. 1 and 6 to 8 respective coaxial bores 7, 7' are provided in the front wall 3 and in the back wall 4 in the middle between the side walls. The center 8 of the bores 7, 7' is equally spaced from the upper and lower edges 9, 9' of the implant and therefore at the center of the front and back wall, respectively. The bores 7, 7' have a first portion 10 with a first bore diameter adjacent to the outside of the front and back wall, respectively, and a following second portion 11 which opens into the cavity 5 and which has a second bore diameter which is slightly less than the first bore diameter. The second portion 11 thereby defines a shoulder.

Each side wall 1, 2 comprises bores 12, 13, and 12', 13', respectively, disposed about centric between the front and back wall and spaced from the upper and lower free edges 9, 9' of the implant, whereby corresponding opposite bores 12, 12' and 13, 13', respectively, of the side walls 1, 2 are coaxial.

Figure 7:
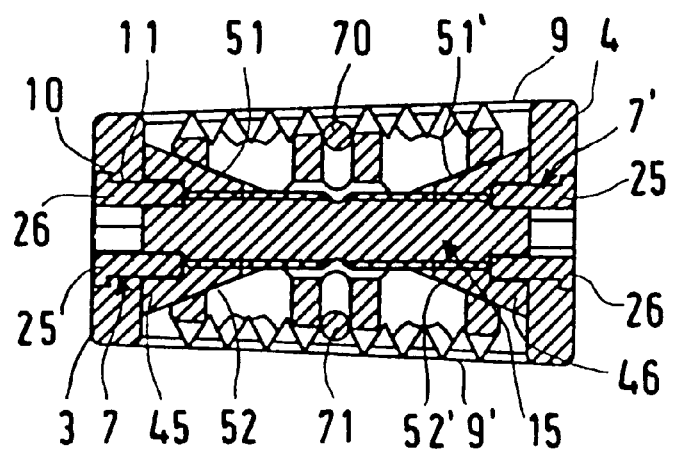
FIG. 7 shows a section through the intervertebrae implant along line IV—IV in FIG. 6, whereby the teeth are in retracted position.
Figure 8:
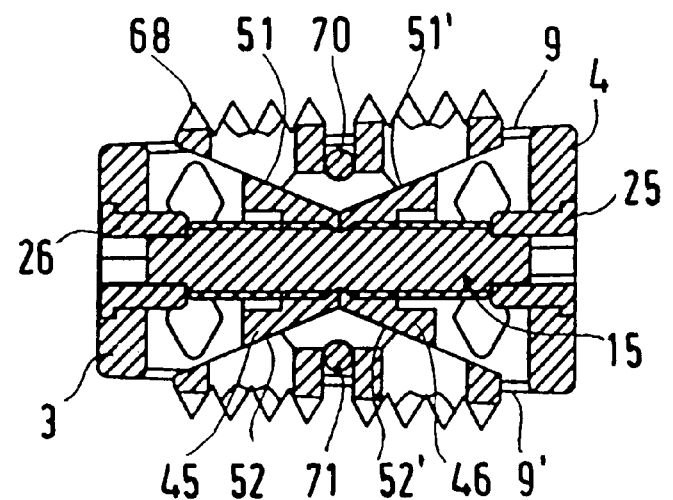
FIG. 8 shows a section through the intervertebrae implant along line IV—IV of FIG. 6, whereby the teeth are in projecting position.

As best seen in the FIGS. 1 and 7 and 8 a threaded spindle 15 is inserted into the pair of coaxial bores 7, 7'. The threaded spindle 5 has a first end 16 and an opposite second end 17. Between the first end 16 and the second end 17 there is a first threaded portion 18 extending from a point somewhat spaced from the first end 16 to almost the center 20 of the threaded spindle and a second threaded portion 19 extending from a point somewhat spaced from the second end 17 to almost the center 20 of the threaded spindle. The thread pitch of the first threaded portion 18 is opposite to the thread pitch of the second threaded portion 19. A first hexagon head 21 and a second hexagon head 22 are formed adjacent to the first end 16 and to the second end 17 of the threaded spindle, respectively.

Figure 6:
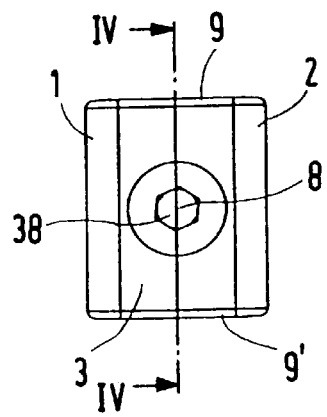
FIG. 6 is a front view of the intervertebrae implant.

As shown in particular in the FIGS. 6 to 8 each end 16, 17 of the threaded spindle 15 is non-rotationally inserted into a corresponding bearing member (or bearing journal) 25, 26 which itself is rotationally supported in a corresponding one of the bores 7, 7' and has its outer face flush with the respective one of the front and back walls. Each bearing member 25, 26 is formed as a part having a first cylindrical portion 27, 27' with a first outer diameter and a following cylindrical section 29, 29' with a second outer diameter which is greater than the first outer diameter. The second portion 29, 29' thereby forms an annular collar projecting beyond the first portion 27, 27'. The diameters of the first and second portions are chosen so as to enable the bearing members 25, 26 to be pushed into the respective bore 7, 7' of the front or back wall whereby the collar of the bearing member formed by the second portion rests on the shoulder of the bore 7, 7' when pushed in. The first portion 27, 27' of the bearing member 25 and 26, respectively, comprises a hexagon bore 34 or 34', respectively, extending from the end of the cylindrical portion 27, 27' opposite to the second portion 29, 29' into the interior of the cylindrical portion 27, 27' and having a depth corresponding to the size of the terminal portion 21, 22 of the threaded spindle 15 for fitting the terminal portions 21, 22 of the threaded spindle 15 thereinto. A coaxial hexagon bore 38, 38' extends from the opposite end of each bearing member 25, 26 towards the first portion 27, 27' for engagement with a hexagon screw driver. Thus, the surgeon can approach and adjust the implant from both sides.

As best shown in the FIGS. 1, 7 and 8 a corresponding wedge member 45 and 46 is provided on each threaded portion 18, 19 of the threaded spindle 15. Each wedge member 45, 46 is defined by a front face 47, 47' and a back face 48, 48' both having a rectangular cross-section and extending parallel to each other and perpendicular to the axis of the spindle, whereby the front face 47, 47' has a smaller cross-section than the back face 48, 48'. The front face is connected to the back face by two opposite trapezoidal side faces 49, 49' and a respective top and bottom face 51, 51' and 52, 52', respectively, of rectangular cross-section to form a wedge.

The wedge member 45 comprises a threaded bore 45 extending through the center of the front and back faces and having an internal thread corresponding to the external thread of the threaded portion 18 of the threaded spindle 15. Likewise, the wedge member 46 comprises a threaded bore 55 extending through the center of the front and back faces and having an internal thread corresponding to the external thread of the threaded portion 19 of the threaded spindle 15. The wedge members 45 and 46 are screwed onto the corresponding threaded portion 18 and 19 of the threaded spindle 15, respectively, in such a position that their corresponding top faces 51, 51' and bottom faces 52, 52' incline towards each other.

A corresponding element 60, 61, respectively, is placed between the mutually inclined top faces 51, 51' and mutually inclined bottom faces 52, 52', respectively, which will be referred to as wedge faces, of the wedge members 45, 46, which element is formed at its lower side facing the wedge members in form of a roof gable with two mutually inclined sloping surfaces 63, 64 and 63', 64', respectively. The angle of inclination of the surfaces 63, 64, and 63', 64', respectively, corresponds to the wedge angle of the wedge members. Each engagement member 60, 61 comprises, on its side facing away from the threaded spindle 15, a surface with a rectangular contour. In longitudinal direction between the front wall and the back wall 3, 4, viewed in the center, each element comprises a U-shaped slit 67 extending parallel to the front wall and back wall 3, respectively, and perpendicular to the surface of the element, the bottom of which is directed to the lower side of the element. The surfaces comprise teeth 68 disposed on the contour of a square, respectively, as shown in particular in FIG. 1 and FIG. 4. A substantially circular depression 69 is disposed between the teeth such that the teeth arranged on the contour of a square form a ring of teeth.

In the middle between front wall and back wall 3, 4 a pin 70, 71 extending parallel to the front wall and the back wall, is extending in a predetermined distance from the bottom face and the top face, respectively, which pin is secured on the opposite side walls. The diameter of the pins 70, 71 is slightly smaller than the diameter of the U-shaped slit 67. As shown in the Figures the pin is located in the U-shaped slit 70, 71 and forms a guidance for the movable elements and simultaneously with its bottom a stop for limitation of the outward movement of the elements. The arrangement of the pin 70, 71 and the depth of the U-shaped slits 70, 71 are matched to each other such that the maximum heights of the outward movement of the respective element over the bottom face and top face is determined by the relative position of the pin and the depth of the slits.

The dimensions of the wedge members 45, 46, the threaded portions 18, 19, the spindle 15 and the engagement members 60, 61, as well as the pitch of the threads is selected so as to allow the engagement members 60, 61 to be displaced from a first position shown in FIG. 7 in which the teeth are located beneath the edge 9, 9', and a second position, which is shown in FIG. 8, in which the teeth project over the respective edge 9, 9' of the implant.

The implant is manufactured from a physically compatible material such as titanium.

Figure 2:
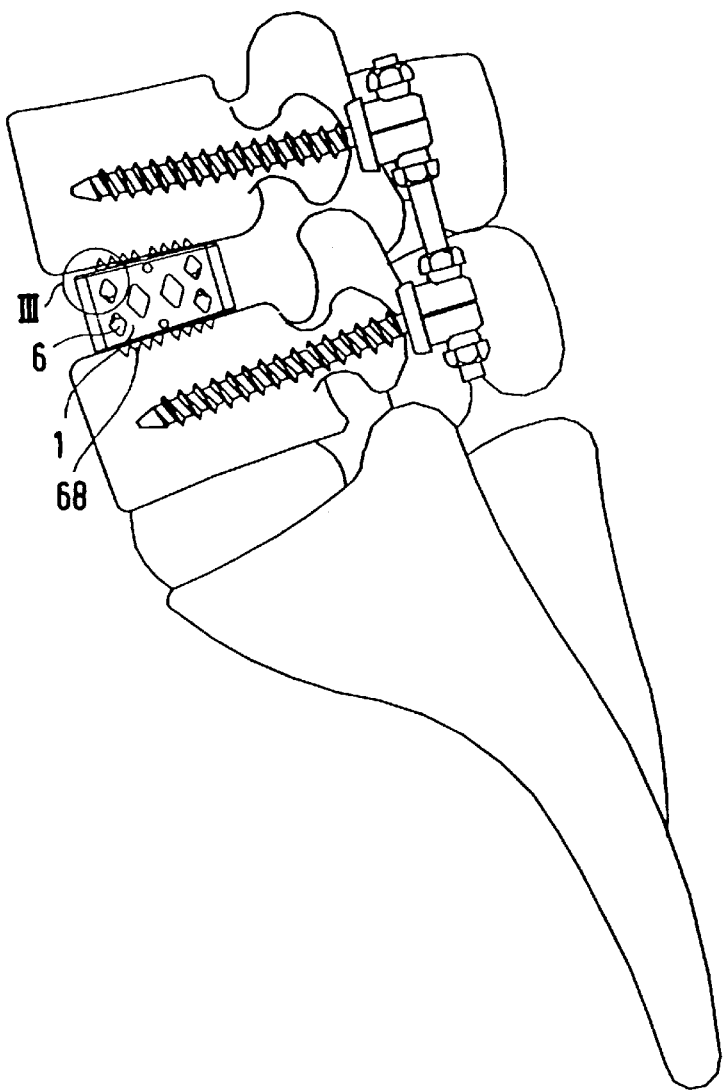
FIG. 2 is a side view of a portion of the spinal column with inserted intervertebrae implant.
Figure 3:
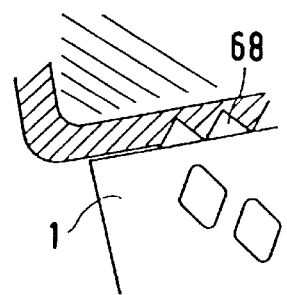
FIG. 3 shows a detail of FIG. 2 on an enlarged scale.
Figure 4:
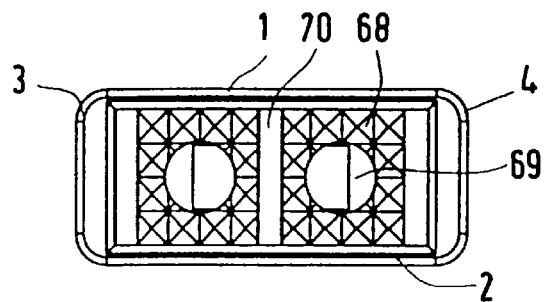
FIG. 4 is a top view of the intervertebrae implant.

In operation first the wedge members 45, 46 are brought into the position shown in FIG. 7, wherein the back faces 48 are in contact with the inner sides of the front and back wall 3, 4 of the implant facing the cavity 5, by rotating the threaded spindle 5 using a hexagon screw driver. This causes each engagement member 60, 61 to take up its lowermost position wherein the teeth 68 do not project beyond the edge of the implant. The implant can therefore easily be inserted into the area between the vertebrae and there is no risk of injuring the soft parts of the end plates of the vertebrae. After having correctly positioned the implant between the vertebrae the two wedge members 45, 46 are moved towards each other by rotating the threaded spindle 15 using a hexagon screw driver, whereby the wedged, mutually inclined surfaces exert a force onto the oblique surfaces 63, 64, and 63', 64' of the corresponding engagement members to raise the same until the teeth 68 project beyond the edge of the implant to thereby clutch the vertebrae, as particularly shown in FIG. 2 and FIG. 3. The lifting movement of the engagement members 60, 61 is limited by the stop formed by the rods 70, 71 to the lift shown in FIG. 8 whereby the teeth 68 of the corresponding engagement member project beyond the edge of the implant.

The transmission of the rotation of the tool through the threaded spindle and the wedge members allows for a precise adjustment of the lift of the engagement members and for an individual adaptation of the implant to the anatomic shape of the end plates of the vertebrae of the individual patient.

By forming the stop of the engagement members 60, 61 as rods 70, 71 engaging the cylinder-segment-shaped recess 67 the engagement members 60, 61 are rotatably supported around the corresponding rod 70, 71 in their uppermost position. This provides for an automatic centering of the engagement members whereby the surface having the teeth 68 follows the anatomic shape of the corresponding end plate of the vertrebrae. The threaded spindle prevents the engagement members from becoming loose by themselves. The engagement members 60, 61 can be retracted only by backward rotation using the tool whereby the pressure exerted by the vertebrae onto the engagement members forces the same into the cavity 5 of the implant. This releases the teeth from the end plate of the vertebra.

Figure 9:
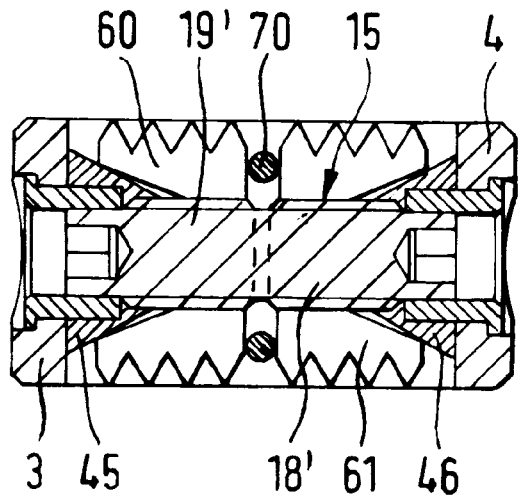
FIG. 9 shows a section corresponding to FIG. 7 of a second embodiment.
Figure 10:
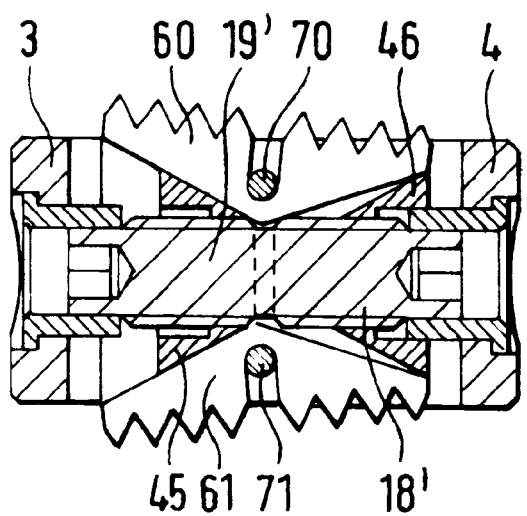
FIG. 10 shows a section corresponding to FIG. 8 of the second embodiment.

In the first embodiments shown in FIGS. 1 to 8 the two wedge members with their wedge angles and the two elements to be pushed out with their wedge faces and angles, engaging therewith, respectively, are matched to each other such that the elements to be pushed out are always aligned parallel to the bottom face and the top face. This embodiment is suitable to be employed every time when the operation is carried through from the ventral side, since the distance of adjacing vertebrae is larger on the ventral side than on the dorsal side. The embodiment shown in FIGS. 9 and 10 is provided in particular for such cases where the element shall be inserted between two adjacent vertebrae from the back. For the further description parts which correspond to each other are indicated with the same reference numeral as in the first embodiment.

In the embodiment the side walls are rectangular-shaped with the consequence that the bottom and top faces extend parallel to each other. As shown in FIG. 9 the wedge members 45, 46 are in the initial position in a position where they are retracted until the stop with respect to the front wall and the back wall, respectively. The elements 60 and 61 are thereby arranged within the cavity enclosed by the side walls and the front and back wall so as to allow insertion of the cuboid the height of which is equal to the height of the gap between adjacent vertebrae at its narrowest position.

Different from the first embodiment the two spindle portions 18', 19' to have not only threads the direction of which is opposite to each other, but also the thread pitches of the two portions are different in addition. As shown in FIG. 10 the thread pitch of the portion 19' is predetermined to be larger than the thread pitch of the portion 18' to such an extent that in the abutting position shown in FIG. 10 where the pins 70, 71 fit closely to the bottom of the U-shaped slits, the elements 60, 61 form a wedge angle against each other with their surfaces which results from the wedge member 45 due to the larger thread pitch of the portion 19' covering a larger distance than the wedge member 46 when rotating the spindle.

Thereby it is achieved that the intervertebrae implant being inserted in the above-described manner in the state shown in FIG. 9 can be brought in the inserted state into the extended position shown in FIG. 10 such that the two elements 60 and 61 are extended corresponding to the inclination of the gap between the two adjacent vertebrae and fit to the two vertebrae. By this it is not necessary that the spindle is rotated until the elements reach their stop at the pin 70, 71, respectively. It is also possible to select intermediate positions.

Modifications of the apparatus are possible. For example, peaks or any other surface structure allowing an engagement with bone material can be provided in place of the teeth 68.

What is claimed is:

1. An intervertebrae implant comprising:
   two spaced side walls,
   a front wall connecting the side walls at one end thereof,
   a back wall connecting the side walls at their other end,
   the walls defining a corresponding space within the walls,
   a bottom face,
   a top face,
   each face extending transversely to said walls,
   at least one member disposed within the space defined by said walls, said member having a surface oriented toward one of the bottom face or the top face, and
   an adjusting element, which is supported in the front wall and the back wall, and which cooperates with the member such that the member is reciprocally movable between a first end position wherein the surface does not project beyond the bottom face or the top face and a second end position wherein the surface at least partially projects outwardly beyond the bottom face or the top face.

2. An intervertebrae implant according to claim 1, further comprising two members.

3. An intervertebrae implant according to claim 1, further comprising a threaded spindle, and
   wherein the adjusting element comprises two wedge members,
   the spindle having two ends and two portions with opposite thread pitch and being provided in the space, one end of the threaded spindle being rotationally supported in the front wall and the other end being rotationally supported in the back wall, and
   wherein the two wedge members are supported within the space in such a manner that, upon rotation of the threaded spindle in one direction, a distance between the wedge members decreases and, upon rotation of the threaded spindle in an opposite direction, the distance between the wedge members increases,
   and said wedge members operate to move the element.

4. An intervertebrae implant according to claim 3, wherein the member comprises two inclined surfaces on a side opposite to said surface and wherein the wedge members engage the inclined surfaces.

5. An intervertebrae implant according to claim 3, wherein each wedge member provides a different wedge angle.

6. An intervertebrae implant according to claim 3, wherein each portion of said spindle has a different thread pitch.

7. An intervertebrae implant according to claim 1, wherein the surface of the member comprises teeth, thereby in use providing for penetration into an adjacent bone material.

8. An intervertebrae implant according to claim 1, further comprising a stop that limits the outward movement of the member.

9. An intervertebrae implant according to claim 8, wherein the stop comprises a pin supported in the side walls and extending substantially parallel to the front wall and the back wall.

10. An intervertebrae implant according to claims 1, wherein the shape of each of the side walls is substantially trapezoidal to provide a truncated wedge-shaped body.

11. An intervertebrae implant according to claim 1, wherein the member is positioned in the second end position in a manner such that said surface is inclined with respect to the bottom face or the top face.

12. An intervertebrae implant comprising:
    two spaced side walls,
    a front wall connecting the side walls at one end thereof, a back wall connecting the side walls at their other end, the walls defining a corresponding space within the walls, a bottom face, a top face, each face extending transversely to said walls, at least one member disposed within the space defined by said walls, said member having a surface oriented toward one of the bottom face or the top face, an adjusting element, which is supported in the front wall and the back wall, and which cooperates with the member such that the member is reciprocally movable between a first end position wherein the surface does not project beyond the bottom face or the top face and a second end position wherein the surface at least partially projects outwardly beyond the bottom face or the top face; and a stop that limits the outward movement of the member;

wherein the stop comprises a pin supported in the side walls and extending substantially parallel to the front wall and the back wall;

wherein said member further comprises a U-shaped slit extending transversely to said surface, said slit cooperating with said pin to limit the outward movement of the member.

13. An intervertebrae implant according to claim 12, further comprising two members.

14. An intervertebrae implant according to claim 12, further comprising a threaded spindle, and wherein the adjusting element comprises two wedge members, the spindle having two ends and two portions with opposite thread pitch and being provided in the space, one end of the threaded spindle being rotationally supported in the front wall and the other end being rotationally supported in the back wall, and wherein the two wedge members are supported within the space in such a manner that, upon rotation of the threaded spindle in one direction, a distance between the wedge members decreases and, upon rotation of the threaded spindle in an opposite direction, the distance between the wedge members increases, and said wedge members operate to move the element.

15. An intervertebrae implant according to claim 14, wherein the member comprises two inclined surfaces on a side opposite to said surface and wherein the wedge members engage the inclined surfaces.

16. An intervertebrae implant according to claim 14, wherein each wedge member provides a different wedge angle.

17. An intervertebrae implant according to claim 14, wherein each portion of said spindle has a different thread pitch.

18. An intervertebrae implant according to claim 12, wherein the surface of the member comprises teeth, thereby in use providing for penetration into an adjacent bone material.

19. An intervertebrae implant according to claims 12, wherein the shape of each of the side walls is substantially trapezoidal to provide a truncated wedge-shaped body.

20. An intervertebrae implant according to claim 12, wherein the member is positioned in the second end position in a manner such that said surface is inclined with respect to the bottom face or the top face.

\* \* \* \* \*